United States Patent

Davis

(10) Patent No.: US 6,543,287 B1
(45) Date of Patent: Apr. 8, 2003

(54) METHOD FOR ACOUSTIC IMAGING BY ANGLE BEAM

(75) Inventor: William R. Davis, Hollywood, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 135 days.

(21) Appl. No.: 09/679,161

(22) Filed: Oct. 5, 2000

(51) Int. Cl.$^7$ .................................................. G01N 9/24
(52) U.S. Cl. ............................ 73/606; 73/612; 73/614; 73/625
(58) Field of Search .......................... 73/606, 607, 610, 73/644, 625, 612, 614, 622, 628, 641, 624; 600/443, 447

(56) References Cited

U.S. PATENT DOCUMENTS

| | | | |
|---|---|---|---|
| 3,720,098 A | * | 3/1973 | Dixon .......................... 73/67.7 |
| 5,216,921 A | * | 6/1993 | Tsuboi .......................... 73/579 |
| 5,431,054 A | * | 7/1995 | Reeves et al. ................. 73/612 |
| 5,483,963 A | | 1/1996 | Butler et al. |
| 5,627,308 A | * | 5/1997 | Dahneke ..................... 73/28.01 |
| 5,714,756 A | * | 2/1998 | Park et al. ................... 250/306 |
| 5,884,239 A | * | 3/1999 | Romanik, Jr. ............... 702/150 |
| 6,005,827 A | | 12/1999 | Hossack et al. |
| 6,016,285 A | | 1/2000 | Wright et al. |
| 6,030,344 A | | 2/2000 | Guracar et al. |
| 6,036,643 A | | 3/2000 | Criton et al. |
| 6,037,579 A | * | 3/2000 | Chan et al. .................. 250/216 |
| 6,137,860 A | * | 10/2000 | Ellegood et al. .............. 378/58 |

* cited by examiner

Primary Examiner—Daniel S. Larkin
Assistant Examiner—Jacques M Saint-Surin
(74) Attorney, Agent, or Firm—Mark O. Glut

(57) ABSTRACT

A method for acoustic imaging by angle beam, which includes generating a sound wave, coupling the wave at an angle to a first surface of a test piece via a physically continuous path. The test piece also has a second surface. The angle being such that the wave progresses along a vectors at an angle to the first surface and the second surface and along the test piece via a plurality of sound reflections reflecting between the first surface and the second surface at points progressing away from the transducer location. The angle also being such that the sound reflections at the first surface produce energy at the first surface such that a first part of every reflection of the wave continues through the first surface in the form of wave through a media toward a CCD acoustic imaging camera, while a second part of the reflection continues along in the test piece. Then focusing the first part of the reflection of the wave such that the first part of the reflection of the wave travels to an imaging area where it is transformed to a video output which displays an internal volume image of the test piece.

15 Claims, 1 Drawing Sheet

METHOD FOR ACOUSTIC IMAGING BY ANGLE BEAM

STATEMENT OF GOVERNMENT INTEREST

Figure 1:
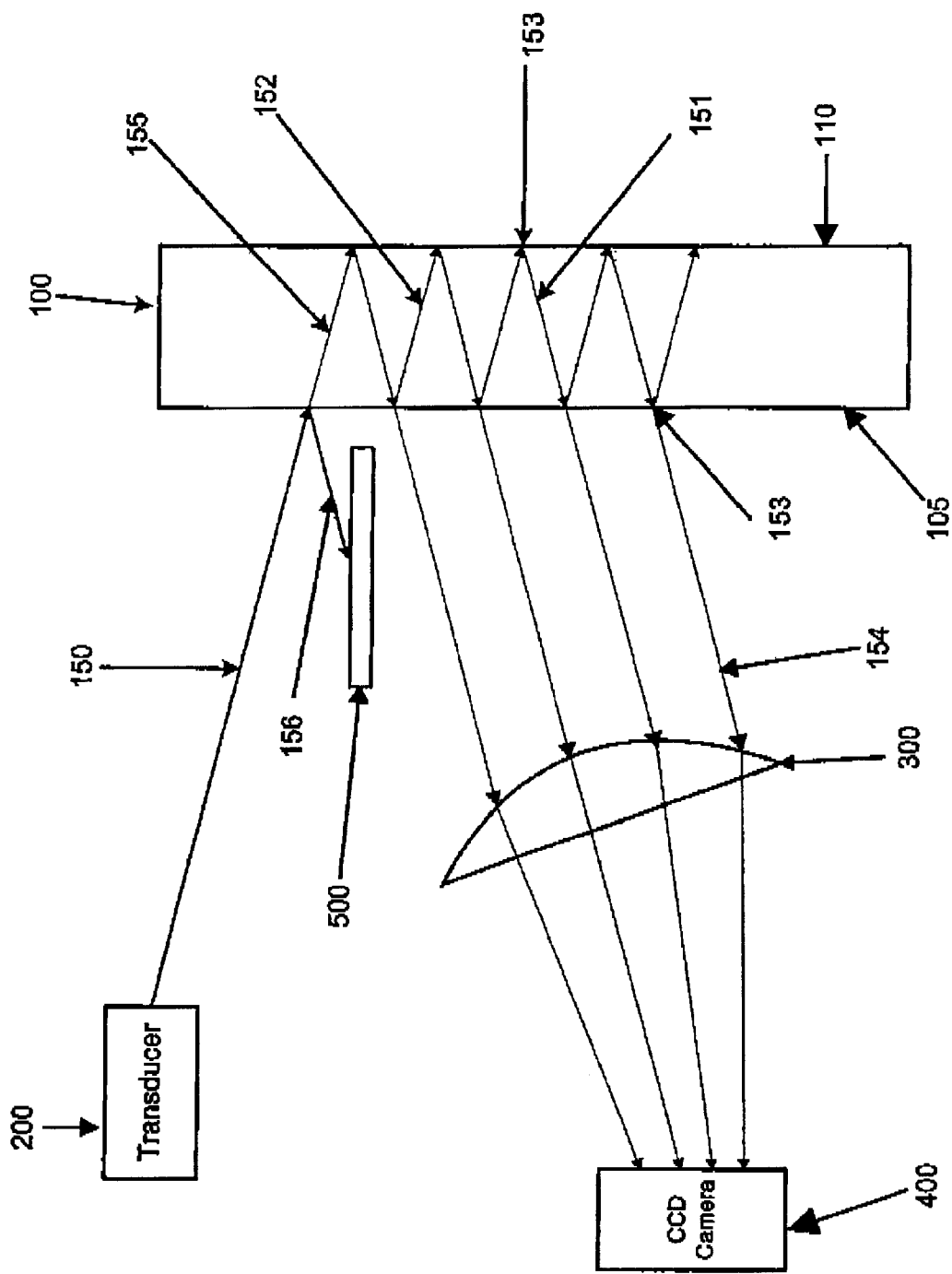

The invention described herein may be manufactured and used by or for the Government of the United States of America for governmental purposes without payment of any royalties thereon or therefor.

BACKGROUND

The present invention relates to a nondestructive technique or method for the inspection of materials. More specifically, but without limitation, the present invention relates to a nondestructive technique or method for the inspection of materials utilizing a method for acoustic imaging by angle beam. The method helps find various imperfections and discontinuities on a material or test piece.

Nondestructive inspection ("NDI") is a field which includes all means of evaluating the quality and strength of materials and structures without adversely affecting their quality, strength or usefulness. NDI usually includes methods recognized by the American Society of Nondestructive Testing. These methods include radiography, eddy current testing, dye penetrant testing, ultrasonic testing, leak testing, thermography, and the like. These methods help find cracks, corrosion, weld flaws, rolling or processing flaws, thickness variations and various other imperfections or discontinuities that may affect quality and strength of a material or structure.

Detection of these types of imperfections or discontinuities is difficult even with all the presently available testing methods. Detection of corrosion and small fatigue cracks is difficult and time consuming when only one side of a material or structure is accessible. In addition, the presently available testing methods do not indicate the type of discontinuity or imperfection. Even ultrasonic inspection with a single crystal search unit does not indicate the type of discontinuity or imperfection.

Another method of nondestructive inspection is the real time imaging of ultrasound waves. Real time imaging of ultrasound waves utilizes a modified Charge Coupled Device ("CCD") camera. The camera provides images with normal television framing rates of 100% of the interior parts. The method utilizes high frequency sound waves instead of ionizing radiation. Sound beams are passed through the work piece being inspected and are partially attenuated by discontinuities and imperfections. The internal volume of the material is therefore imaged as in radiography (volumetric inspection). This then provides a shadowgraph display similar to a real time X-ray except that no ionizing radiation is present. Unlike radiographic (X-ray) methods, sound waves are strongly blocked by cracks, voids and other interfacial discontinuities. This provides higher sensitivity to critical and potentially dangerous discontinuities or imperfections. The real time imaging of ultrasonic waves method either passes the sound beam entirely through the material or structure, or introduces the sound beam from the front of the material or structure (perpendicular to it). It then images the part of the beam reflected back to the camera by internal discontinuities or imperfections. These methods are successful in thick structures or when the beam can be arranged to pass through the structure or material from one side to the other (through transmission). These methods have difficulty inspecting very thin objects or when one side of the material or structure is not accessible.

Thus, there is a need in the art to provide a method for acoustic imaging by angle beam that incorporates the listed benefits without the limitations inherent in present methods. For the foregoing reasons, there is a need for a method of inspection that can quickly inspect thin material for discontinuities or imperfections. In addition, there is also a need for a method of inspection that allows inspection of a material when both sides of the material are not accessible.

SUMMARY

The instant invention is directed to a method for acoustic imaging by angle beam that satisfies the needs enumerated above and below.

The present invention is directed to a technique or method for the inspection of materials, specifically a test piece with a first surface and a second surface. The invention utilizes real time ultrasonic imaging in a new and unique way. An ultrasonic sound wave is introduced at an angle to the first surface of the test piece or piece to be inspected. The wave is at an angle sufficient to cause it to progress through the test piece by bouncing forward consecutively between the first and second surfaces of the test piece. The wave enters the test piece, is refracted, and proceeds to the second surface (the surface furthest from a CCD acoustic imaging camera) at some non-vertical angle and reflects to the first surface (the surface nearest the CCD acoustic imaging camera). Part of the wave refracts through the first surface to the CCD acoustic imaging camera while another part reflects and travels to the second surface. This is repeated and the wave moves down the test piece in a series of bounces between surfaces with a proportion refracting through the first surface at each bounce. The portion of the beam that refracts through the first surface is focused to an imaging area in the CCD acoustic imaging camera, which transmits the wave to a video output. The video output displays the internal volume of the test piece. The video output further displays all the imperfections and discontinuities of the test piece. It allows a user to determine the location and type of imperfection or discontinuity.

It is an object of the invention to provide a method for fast inspection of a thin material. It is also an object of the invention to provide a method where the test piece can be inspected for corrosion and cracks when both surfaces of the thin material are not accessible.

It another object of the invention to provide a method for volumetric or three-dimensional inspection. In addition, it is also an object of the invention to provide a method of inspection that indicates the type of discontinuity or imperfection.

DRAWINGS

These and other features, aspects and advantages of the present invention will become better understood with reference to the following description and appended claims, and accompanying drawing wherein:

FIG. 1 is a representation of one of the embodiments of the method of acoustic imaging by angle beam.

DESCRIPTION

The preferred embodiment of the present invention is illustrated by way of example below and in FIG. 1. The preferred embodiment of the method for acoustic imaging by angle beam includes sending a timing signal from a Charge Coupled Device ("CCD") acoustic imaging camera 400 to a digital delay circuit. The digital delay circuit delays the timing signal for a programmed amount of time and then transmits the timing signal to an electronic pulser circuit.

The electronic pulser circuit generates an electronic pulse of programmed amplitude and shape, and the electronic pulse is transmitted to a transducer 200. The electronic pulse can be transmitted to the transducer 200 via a wire, conduit, channel, any electric/electronic transmitting material, or the like.

The CCD acoustic imaging camera 400 is a Charge Coupled Device camera that is modified to detect pressure and/or sound waves rather than light waves. The Charge Coupled Device uses integrated circuitry to transfer a signal along a row of discrete picture elements (or pixels). The CCD acoustic imaging camera 400 can be an adaptation of an infrared focal plane array and electronics. The focal plane array can be a hybrid fabricated from polyvinyl difluoride spun coated on to a CCD imaging array.

A transducer 200 is any device or element that converts an input signal into an output signal of a different form. An ultrasonic transducer will provide the best results. Ultrasonic transducers can be piezoelectric, electromagnetic, electrostatic, magnetostatic, laser, optical, any other type transducer, or the like. The preferred embodiment includes a piezoelectric transducer and typically consists of a piezoelectric element in the form of a wafer cut from a single (natural) crystal. The crystal vibrates preferentially at the natural resonant frequency of the crystal as fabricated in a metallic housing.

The electronic pulse of programmed amplitude and shape is tailored to the type of modified CCD imaging array being utilized. A CCD imaging array that is bipolar and is affected by negative pressure (losing charge or energy) requires a longer positive pressure wave to maximize signal intensity. A CCD imaging array, which can differentiate between positive and negative pressure, can change the sign of the negative pressure to make the two additive. It may utilize sound pressure in the form of a true sine wave. Any electronic circuit that outputs voltage and wave shape can be used.

The transducer 200 changes the electronic pulse into a sound wave 150. This is done via piezoelectric effect, which is a phenomenon in which an impressed electronic signal produces a mechanical vibration. As seen in FIG. 1, the test piece 100 has a first surface 105 and a second surface 110. The sound wave 150 is coupled or projected at an angle to the first surface 105 of a test piece 100 via a physically continuous path or conductor. A physically continuous path is a way or course traversed by the sound wave 150. In a physically continuous path the way or course is typically a material, matter, a substance, a fluid (gas or liquid), or the like. In the preferred embodiment, the physically continuous path is composed of a solid or a liquid. When the continuous path is a liquid, the sound wave 150 is a compression wave. When the physically continuous path is a solid, the sound wave 150 is a physical (strain) wave.

As shown in FIG. 1, typically the first surface 105 and the second surface 10 of the test piece 100 are parallel. However, the method is also effective when the surfaces are not parallel. The first surface 105 is typically the surface closest to the CCD acoustic imaging camera 400, while the second surface 110 is the surface farther from the CCD acoustic imaging camera 400. The sound wave 150 is coupled to the first surface 105 of the test piece 100 at an angle such that the sound wave 150 progresses into the test piece 100 along vectors at an angle to the first surface 105 and the second surface 110 and along the test piece 100 via a plurality of sound reflections 153 reflecting between the first surface 105 and the second surface 110 at points progressing away from the transducer 200 location. FIG. 1 shows the vectors towards the second surface 152 and the vectors towards the first surface 151. When the wave 150 is coupled or projected to the [top] first surface 105 of the test piece 100 the sound wave 150 follows the normal laws of physics for wave propagation. Part of the sound wave 150 refracts through the first surface 105 away from the test piece 100 while another part of the wave 150 reflects from to the first surface 105 back to the second surface 110. Because the wave 150 follows the normal laws of physics for wave propagation this pattern is repeated until the wave 150 passes through the entire test piece 100. The angle is also such that the physical (strain) or compression wave across the test piece 100 by a plurality of sound reflections 153 from the first surface 105 and the second surface 110 of the test piece 100 produces energy (a wave) in the form of a sound wave at the first surface 105, such that a first part of every reflection 154 of the plurality of sound reflections continues through the first surface 105 of the test piece 100 through a media toward the CCD acoustic imaging camera 400, and a second part of every reflection 155 of the plurality of sound reflections reflects from the first surface 105 toward the second surface 110. This pattern is repeated until the sound wave passes through the entire test piece 100.

In the preferred embodiment, when the sound wave 150 is initially projected toward the test piece 100, the first part of the first reflection of the plurality of sound reflections 156 is blocked by imposing a barrier or sound baffle 500. The sound baffle 500 may be placed near the point of first incidence. In certain instances, the first part of the first reflection 156 can be of much greater amplitude and may prevent detection of second surface reflections.

The media is a path or conductor for sound/ultrasound waves. The media may be liquid or solid. A media is used because the media enables travel of the waves to the point of interest without undue attenuation. Any type of liquid may be used such as water, glycerin, grease, alcohol, oil, any kind of paste (such as wallpaper paste or toothpaste), any type of gel, or the like. Water is usually the easiest and most convenient. In the preferred embodiment, the liquid must contain no bubbles, which can block or distort the wave. Any solid may be used, but using a solid that is the same material as the test piece produces the best results, because there is minimal refraction or reflection of the sound wave at the interface of the test piece and media. The media and continuous path is usually the same material or liquid.

In the preferred embodiment, the physical (strain) or compression wave that is exiting the test piece 100 (the first part of every reflection 154 of the plurality of sound reflections) is focused by an acoustic lens 300 such that the wave 150 travels to an imaging area within the CCD acoustic imaging camera 400, where it is transformed by readout electronics into electronic signals. The physical (strain) or compression wave can also be recorded from a pressure sensitive device such as a pressure sensitive liquid crystal display in contact with the surface or by focusing the energy upon it via a lens.

An acoustic lens 300 is a lens for focusing acoustic waves. The acoustic lens 300 can be a refractor or reflector of appropriate shape. The refractor can be circular or non-circular in contour. The reflector can also be circular or non-circular in contour. An acoustic lens 300 can focus a sound wave onto a specific point, allowing a very weak sound to be more easily heard. It also can be used to focus sound from one point onto another and to form a clear sound. The acoustic lens 300 is used to directly focus the sound wave 150 onto the imaging area within the CCD acoustic imaging camera 400 and will allow a weak signal to be more easily heard. In the preferred embodiment, the acoustic lens 300 may be fabricated from any homogeneous material that does not cause random distortions of waves. The acoustic lens 300 can be manufactured from plastic, glass, ceramic, Lucite (™), or the like.

The electronic signals may be analog and/or digital signals. The electronic signals are then transmitted to a video output such that the video output displays an image of the internal volume of the test piece 100. The electronic signals can also be transmitted to a Digital Signal processor ("DSP") frame grabber and user interface. The video output can also electronically communicate with a computer. The computer may, but without limitation, enhance the image, shift the image, focus the image on a particular point or record the image for future reference. The computer may also have the ability to measure and record the size and type of imperfection or discontinuity found on the test piece.

The CCD camera 400 may be set to be activated for a limited duration of time. In this embodiment, the total amount of delay time (or programmed amount of time) can be the time required for the electronic pulser circuit to receive a sync pulse from the CCD camera 400, delay for a preprogrammed amount of time (which can be any chosen amount of time), generate an electrical pulse, send the pulse to the transducer 200, for the transducer 200 to change the electrical signal into a physical or compression wave, for the wave 150 to travel to the test piece 100, through the test piece 100, through the acoustic lens 300 and to the CCD acoustic imaging camera 400. The time delay value thus depends on the velocity of sound in the media, in the test piece 100, in the continuous path and the distance traveled, along with the time to generate and transform electrical pulses into physical or compression waves. The CCD acoustic imaging camera 400 is activated to look for a short sequence of physical or compression waves at the time when the waves arrive from the media. The limited duration of time during which the camera is activated to look for waves makes the adjustment of the delay time critical otherwise no image will be generated.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for acoustic imaging by angle beam, the method generating an internal image of a test piece, the test piece having a first surface and a second surface, the method for acoustic imaging by angle beam comprises:

(a) generating a sound wave via a transducer;

(b) coupling the sound wave to the test piece at an angle to the first surface of the test piece via a physically continuous path, the angle being such that the sound wave progresses into said test piece along vectors angled to said first surface and said second surface and along said test piece via a plurality of sound reflections reflecting between said first surface and said second surface at points progressing away from the transducer location, said angle also being such that the sound reflections at said first surface produce energy at said first surface such that a first part of every reflection of the plurality of sound reflections continues through said first surface in the form of a wave through a media toward a CCD acoustic imaging camera, while a second part of every reflection of the plurality of sound reflections reflects from said first surface toward said second surface and continues along in said test piece;

(c) focusing the waves that continue through said first surface to an imaging area in the CCD acoustic imaging camera; and (d) transforming said waves focused to the imaging area to a video output via said CCD acoustic imaging camera such that said video output displays an internal volume image of said test piece.

2. The method of claim 1, wherein the sound wave is generated by (a) sending a timing signal from the CCD acoustic imaging camera to a digital delay circuit which delays the timing signal for a programmed amount of time and then transmits the timing signal to an electronic pulser circuit;

(b) generating an electronic pulse of programmed amplitude and shape by the electronic pulser circuit;

(c) transmitting the electronic pulse to a transducer; and, (d) changing the electronic pulse via the tranducer into a sound wave.

3. The method of claim 2, wherein the focusing of the first part of every reflection of the plurality of sound reflections is done by an acoustic lens.

4. The method claim of claim 3, wherein the programmed amount of delay time is an amount of time required for the electronic pulser circuit to generate an electrical pulse, send the pulse to the transducer, for the transducer to change the electrical signal into a sound wave, for the sound wave to travel to the test piece, through the test piece, through the acoustic lens and to the CCD acoustic imaging camera.

5. The method of claim 1, wherein the continuous path is a liquid wherein the sound wave produced is a compression wave.

6. The method of claim 5, wherein the media is a solid.

7. The method of claim 6, wherein the media is the same material as the test piece.

8. The method of claim 5, wherein the media is a liquid.

9. The method of claim 8, wherein the media and continuous path are the same liquid.

10. The method of claim 1, wherein the continuous path is a solid wherein the sound wave produced is a physical (strain) wave.

11. The method of claim 10, wherein the media is a solid.

12. The method of claim 11, wherein media is the same material as the test piece.

13. The method of claim 12, wherein media and continuous path are the same material.

14. The method of claim 10, wherein media is a liquid.

15. The method of claim 1, wherein the plurality of sound reflections has a first reflection, the first part of the first reflection of the plurality of sound reflections is blocked by imposing a sound baffle.

* * * * *

UNITED STATES PATENT AND TRADEMARK OFFICE
CERTIFICATE OF CORRECTION

PATENT NO. : 6,543,287 B1
DATED : April 8, 2003
INVENTOR(S) : William R. Davis

It is certified that error appears in the above-identified patent and that said Letters Patent is hereby corrected as shown below:

<u>Title page,</u>
Item [57], ABSTRACT,
Line 5, delete "a" after the word "along."

<u>Column 3,</u>
Line 56, should read -- second surface 110 -- not "second surface 10."

<u>Column 4,</u>
Line 4, delete "[top]."

Signed and Sealed this

Twenty-ninth Day of July, 2003

JAMES E. ROGAN
*Director of the United States Patent and Trademark Office*